United States Patent
Stetsko et al.

(10) Patent No.: US 11,596,736 B1
(45) Date of Patent: *Mar. 7, 2023

(54) DUAL NEEDLE DELIVERY SYSTEM THAT CONNECTS AND DEPLOYS NEEDLES OF A MEDICATION DELIVERY DEVICE

(71) Applicant: Gina G. Stetsko, Doylestown, PA (US)

(72) Inventors: Gina G. Stetsko, Doylestown, PA (US); Gregg A. Henderson, Munroe Falls, OH (US); Jason A. Belton, Norton, OH (US); Rick W. Walker, Stow, OH (US)

(73) Assignee: Maia Pharmaceuticals, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/885,489

(22) Filed: Aug. 10, 2022

Related U.S. Application Data

(63) Continuation of application No. 17/546,030, filed on Dec. 8, 2021, now Pat. No. 11,439,750.

(51) Int. Cl.
*A61M 5/158* (2006.01)
*A61M 5/145* (2006.01)
(Continued)

(52) U.S. Cl.
CPC ............ *A61M 5/158* (2013.01); *A61J 1/1468* (2015.05); *A61M 5/14248* (2013.01);
(Continued)

(58) Field of Classification Search
CPC .............. A61M 5/158; A61M 5/14248; A61M 5/16804; A61M 2005/14252;
(Continued)

(56) References Cited

U.S. PATENT DOCUMENTS 5,957,895 A 9/1999 Sage et al.
6,074,369 A 6/2000 Sage et al.
(Continued)

FOREIGN PATENT DOCUMENTS

WO 2020052723 A1 3/2020

OTHER PUBLICATIONS

International Search Report and the Written Opinion issued in PCT/US2022/049035, dated Jan. 4, 2023 (6 pages).

*Primary Examiner* — Nathan R Price
*Assistant Examiner* — Justin L Zamory
(74) *Attorney, Agent, or Firm* — Arc IP Law, PC; Joseph J. Mayo

(57) ABSTRACT

A medication delivery patch that is applied to the skin and activated to deliver a medication or other fluid into or through the skin. The patch may be completely mechanically driven, with no electronic components, for low cost, safety, and reliability. Pressing an activation button may set in motion a sequence of mechanical events that result in a needle exiting the patch into the skin of the user, and flow of fluid from an internal pouch in the patch into the user. When delivery is complete, another sequence of mechanical events may occur to retract the needle from the skin and stop the flow of fluid, and to show a visible indicator that delivery is complete. The patch may contain a fluid channel, such as a microfluidic channel, that controls the rate and time of delivery; this channel can be configured or selected for different medications or use cases.

10 Claims, 15 Drawing Sheets

(51) Int. Cl.
*A61M 5/142* (2006.01)
*A61J 1/14* (2023.01)

(52) U.S. Cl.
CPC ............ *A61M 2005/14252* (2013.01); *A61M 2005/1585* (2013.01); *A61M 2005/1586* (2013.01); *A61M 2205/3386* (2013.01)

(58) Field of Classification Search
CPC .......... A61M 2005/1583; A61M 2005/14506; A61M 2005/1585; A61M 2005/1586; A61M 2205/3386; A61M 2205/583; A61J 1/14668
See application file for complete search history.

(56) References Cited

U.S. PATENT DOCUMENTS

| | | |
|---|---|---|
| 7,918,843 B2 | 4/2011 | Genosar et al. |
| 8,439,838 B2 | 5/2013 | Mogensen et al. |
| 8,905,974 B2 | 12/2014 | Carter et al. |
| D863,546 S | 10/2019 | Converse et al. |
| 2004/0104160 A1* | 6/2004 | Scagliarini ............ A61M 5/165 210/321.75 |
| 2007/0203454 A1 | 8/2007 | Shermer et al. |
| 2008/0051714 A1 | 2/2008 | Moberg et al. |
| 2009/0131860 A1 | 5/2009 | Nielsen |
| 2011/0054285 A1 | 3/2011 | Searle et al. |
| 2013/0018326 A1 | 1/2013 | Hooven |
| 2013/0123709 A1 | 5/2013 | Carter et al. |
| 2017/0326292 A1 | 11/2017 | Sage et al. |
| 2019/0022305 A1 | 1/2019 | Schmidt |
| 2020/0214625 A1 | 7/2020 | Hooven et al. |
| 2020/0384195 A1 | 12/2020 | Moeller |

* cited by examiner

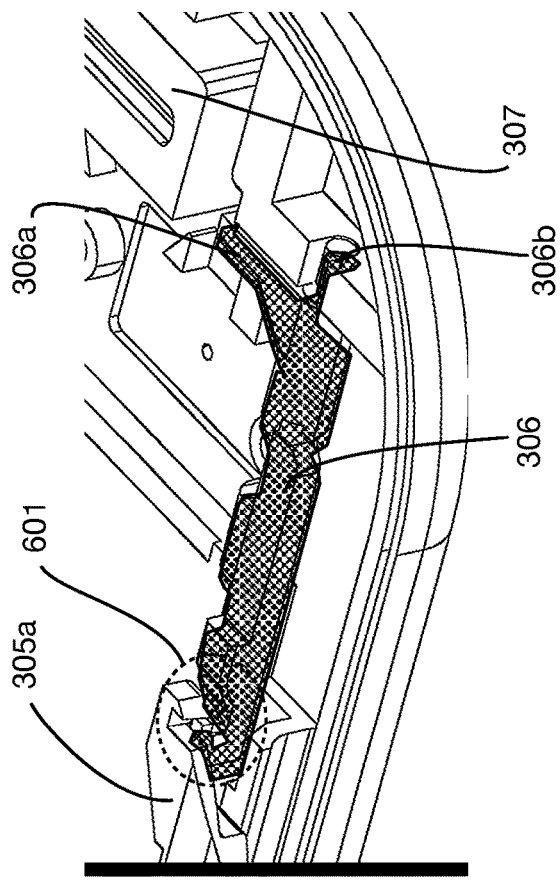
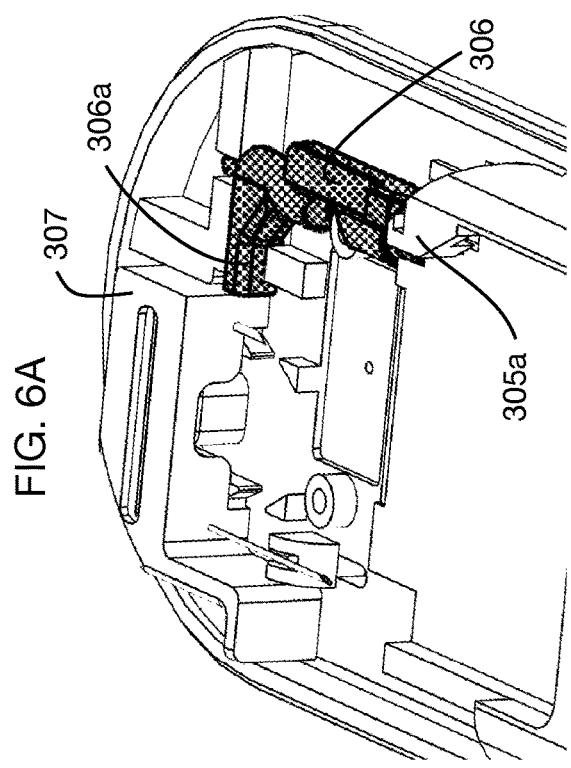
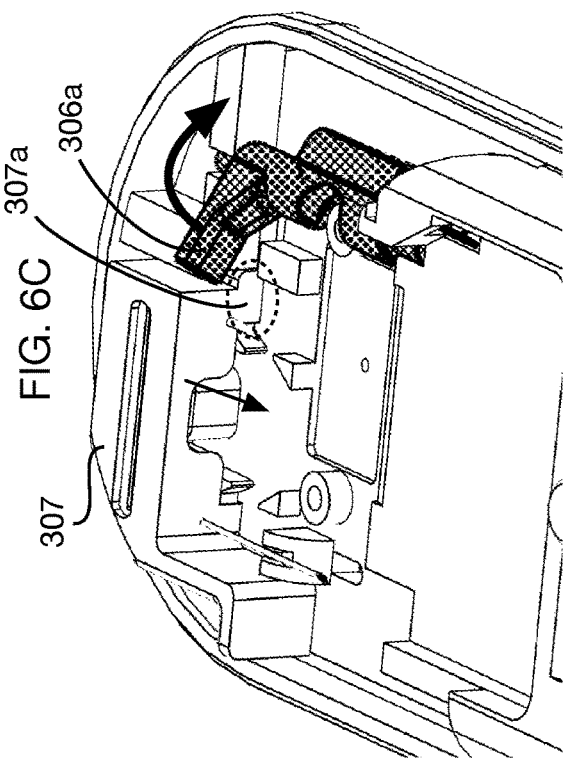

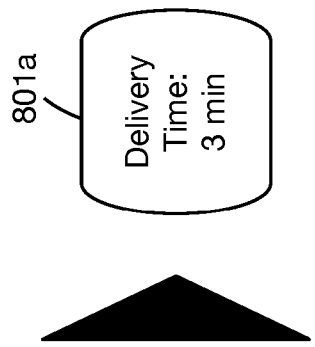
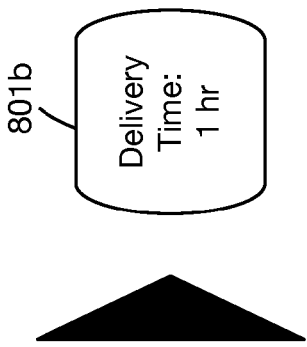
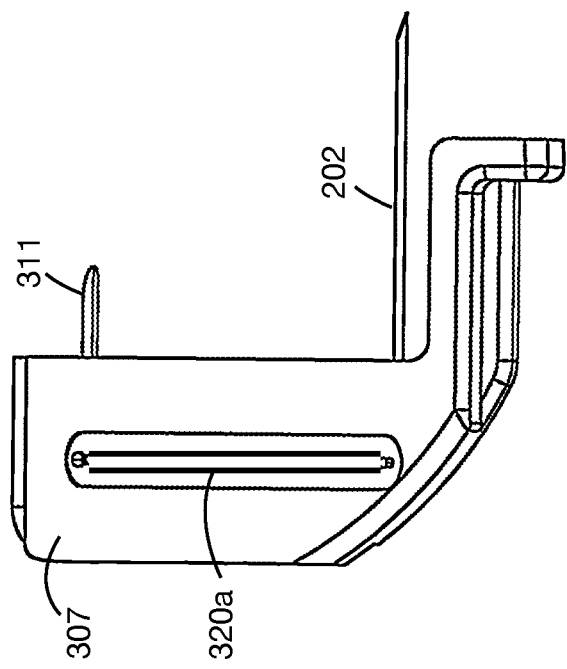
FIG. 8A
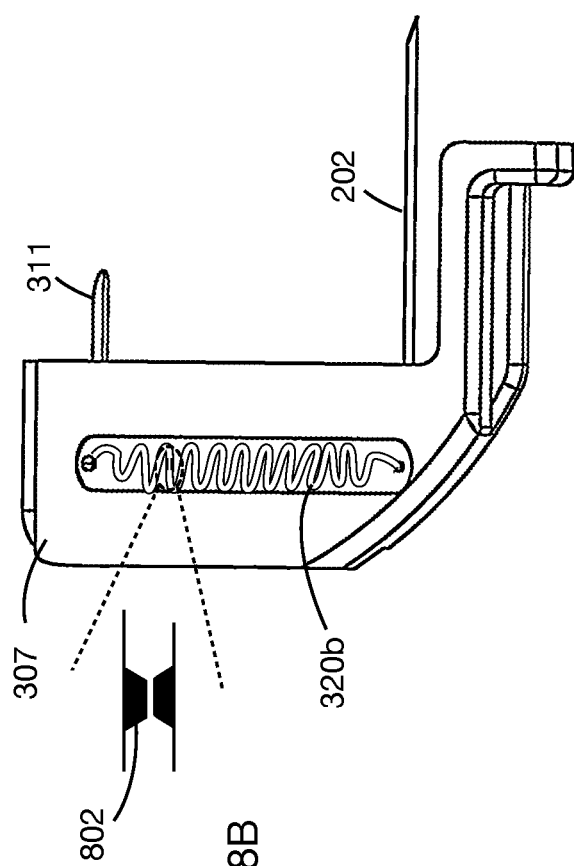
FIG. 8B

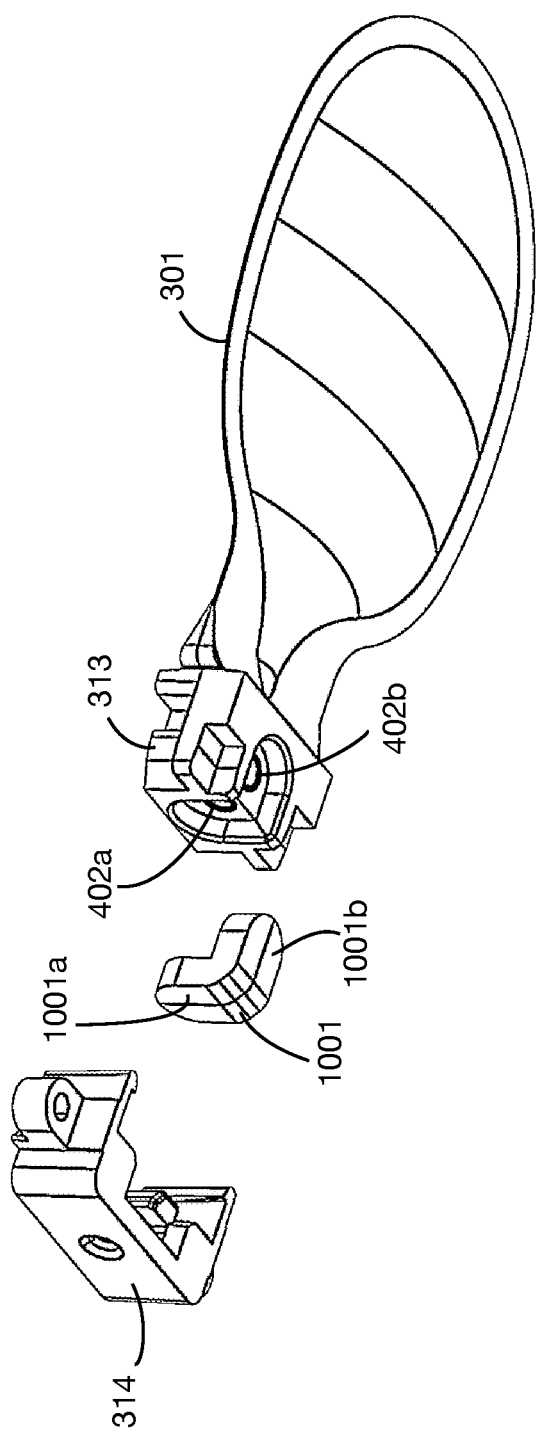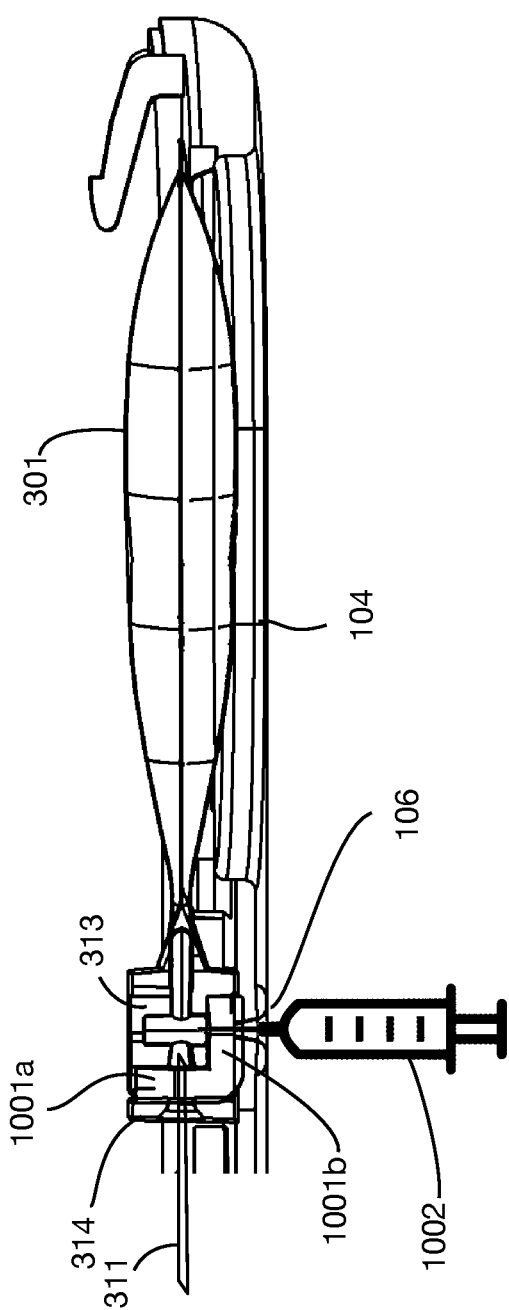
FIG. 10A
FIG. 10B

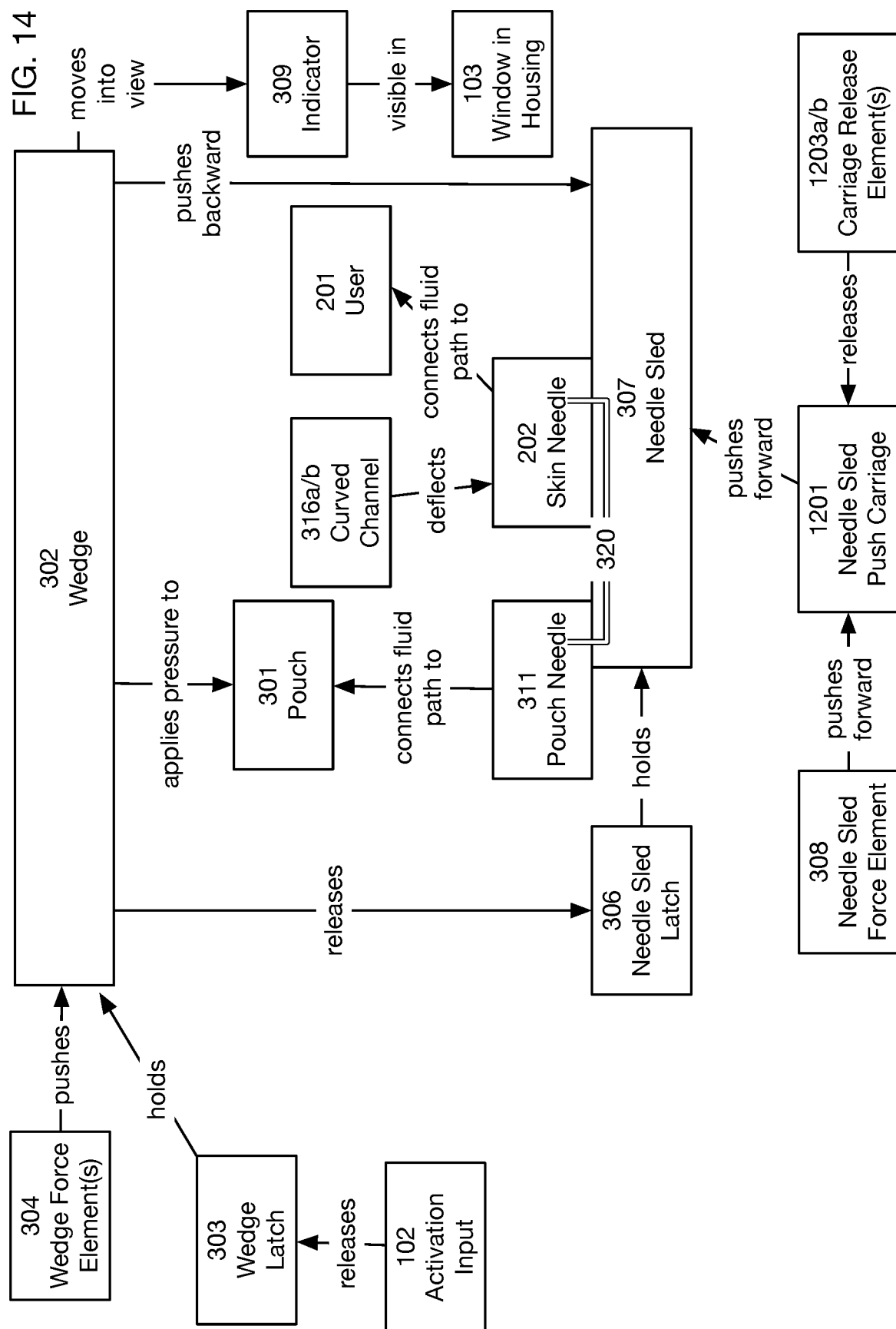

DUAL NEEDLE DELIVERY SYSTEM THAT CONNECTS AND DEPLOYS NEEDLES OF A MEDICATION DELIVERY DEVICE

This application is a continuation of U.S. Utility patent application Ser. No. 17/546,030, filed 8 Dec. 2021, the specification of which is hereby incorporated herein by reference.

BACKGROUND OF THE INVENTION

Field of the Invention

One or more embodiments of the invention are related to the field of medication delivery devices. More particularly, but not by way of limitation, one or more embodiments of the invention enable a mechanically driven medication delivery patch.

Description of the Related Art

Wearable drug delivery devices known in the art use electronic controls and electrically powered motorized pumps and valves. Some of these devices provide Bluetooth connectivity and control interfaces via mobile phones. While these devices provide significant capabilities, they are typically expensive because of their sophisticated components and difficult to utilize. In addition, their reliance on electronics and electrical power may reduce device reliability and longevity.

Some wearable drug delivery devices without electronic components are known in the art but they present problems and challenges in certain applications. The device described in United States Patent Publication US20200384195A1 ("Moeller") uses osmotic pressure to drive medication from the patch to the needle in the user's skin; therefore it is not purely mechanical. This device contains a pre-filled cartridge containing the medication. The device described in United States Patent Publication US20130123709A1 ("Carter") is manually actuated by a user; the user pushes on actuator buttons to drive medication from the device into the needle. This device is intended for self-administration of a short bolus dose of insulin. The user fills the device periodically from a syringe.

There is a need for wearable drug delivery devices that work mechanically and that provide options for either short-term bolus delivery or infusion over an extended period. There is a need for mechanical wearable devices that can be either factory-filled or filled at the point of distribution such as at a pharmacy.

For at least the reasons described above there is a need for a mechanically driven medication delivery patch with added flexibility in application. There are several other embodiments and features that are novel and disclosed in the specification that will become apparent as the device operation is described.

BRIEF SUMMARY OF THE INVENTION

One or more embodiments described in the specification are related to a mechanically driven medication delivery patch. The patch may be placed on the skin and upon activation it may extend a needle into the skin and deliver a contained medication or other fluid to the user, using stored mechanical energy and mechanical force.

One or more embodiments of the invention may include a patch with a bottom surface, a top cover, and a pouch between the top cover and the bottom surface that is configured to contain fluid to be delivered to a user. The bottom surface of the patch may be configured to be attached to the user's skin. There may be an activation button or other activation input. The activation button may be accessible through the top cover. The patch may include a wedge that moves after activation from an initial position to an end-of-delivery position, and then from the end-of-delivery position to an end-of-travel position. The wedge may be held in its initial position by a latch prior to activation. A force element may apply force to the wedge to cause it to move. The wedge applies pressure to the fluid in the pouch as it moves between the initial position and the end-of-delivery position. In one or more embodiments, the wedge may be any type of element that applies pressure to the fluid in the pouch; for example, it may be a roller that rolls across the pouch. The patch may also include a needle sled with a pouch needle configured to penetrate a pouch septum that is in contact with the fluid in the pouch, a skin needle configured to penetrate the user's skin, and a fluid channel that couples the interior of the pouch needle and the interior of the skin needle. The needle sled may be configured to move between a retracted position and a deployed position. A needle sled latch may hold the needle sled latch in the retracted position. A needle sled force element may apply force to the needle sled to cause it to move to the deployed position and to cause the pouch needle to penetrate the pouch septum, the skin needle to penetrate the user's skin, and fluid to flow from the pouch through the pouch needle, through the fluid channel, and through the skin needle into the user. When the activation button is pressed, the wedge latch may be released, allowing the wedge to move from its initial position, and the needle sled latch may be released, allowing the needle sled to move to its deployed position. When the wedge reaches its end-of-delivery position, the wedge may apply force to the needle sled to move the needle sled towards its retracted position, and to retract the pouch needle from the pouch septum and retract the skin needle from the user's skin and into the interior of the patch.

In one or more embodiments, the patch may contain no electronic components.

In one or more embodiments, the pouch may include a flexible material.

One or more embodiments may have a plate between the wedge and the pouch; the wedge may apply force to the plate and the plate may transfer this force to the pouch to apply pressure to the enclosed fluid.

One or more embodiments may have a fill port coupled by a fill channel to the pouch, and a fill septum that closes the fill port and is configured to be penetrated by a fill needle to fill the pouch with fluid.

One or more embodiments may have a delivery complete indicator that provides a visual indication that the wedge has reached its end-of-travel position. In one or more embodiments the top cover of the patch may have a window through which the delivery complete indicator is visible when the wedge reaches its end-of-travel position. The delivery complete indicator may be coupled to or integrated into the wedge.

In one or more embodiments, the fluid channel in the needle sled may have shape, length, diameter, materials, valves, or flow restrictors, or any combination thereof, to provide a desired rate of delivery of the fluid to the user over a desired time period between the start time when the activation button is pressed and a finish time when the wedge reaches its end-of-travel position. In one or more embodiments, the fluid channel may include a microfluidic channel. For example, in one or more embodiments one or more of the shape, length, diameter, valves, and flow restrictors of the fluid channel may be configured to select a desired time period in a range between 10 seconds and 7 days.

Illustrative force elements that may be used in one or more embodiments may include springs. For example, the wedge force element may include one or more wedge springs, and the needle sled force element may include one or more needle sled springs.

In one or more embodiments, the activation button may have one or more activation button extensions that extend into the interior of the patch to contact the wedge latch when the button is pressed, applying force to the wedge latch to release it.

In one or more embodiments, the wedge may be configured to contact a needle sled release element that is coupled to the needle sled latch, and to transmit a portion of the force applied by the wedge force element to the needle sled release element to release the needle sled latch. For example, when the wedge contacts the needle sled release element, the needle sled release element may pivot to release the needle sled latch.

One or more embodiments may have a needle sled push carriage that is coupled to the needle sled force element and that is releasably coupled to the needle sled. This carriage may be configured to transmit force from the needle sled force element to the needle sled. In one or more embodiments the needle sled push carriage may be configured to detach from the needle sled when the needle sled reaches its deployed position. For example, the patch may have one or more carriage release elements configured to contact one or more portions of the needle sled push carriage when the needle sled reaches its deployed position and to decouple the needle sled push carriage from the needle sled.

In one or more embodiments the gauge of the pouch needle may be between 18 gauge and 27 gauge, inclusive and the gauge of the skin needle may be between 25 gauge and 34 gauge inclusive.

One or more embodiments may have a curved channel through which the skin needle travels when the needle sled moves from the retracted position to the delivery position. This channel may cause the skin needle to change orientation from substantially parallel to the skin in the retracted position to non-parallel with the skin in the deployed position. When the needle sled is in the deployed position, the angle between the skin and the skin needle may be greater than or equal to 45 degrees and less then 90 degrees in one or more embodiments.

One or more embodiments may have a feature or features that prevent the needle sled from moving prior to user activation of the patch; this may prevent accidental movement due to shock or vibration.

One or more embodiments may have a feature or features that prevent the activation button from firing accidentally (prior to the user pressing the button) due to shock or vibration.

One or more embodiments may incorporate a hydrophobic vent to vent air from the drug container as well as a portion of the fluid pathway.

BRIEF DESCRIPTION OF THE DRAWINGS

The above and other aspects, features and advantages of the invention will be more apparent from the following more particular description thereof, presented in conjunction with the following drawings wherein:

FIGS. 6A, 6B, and 6C show a mechanism that may be used to release a needle sled that connects and deploys pouch and skin needles when the wedge begins to move after activation. FIG. 6A shows the wedge and needle sled latch prior to activation; FIG. 6B shows a different view of these elements to illustrate how the wedge pivots the latch, and FIG. 6C shows the needle sled latch in the released position.

FIGS. 8A and 8B illustrate selection of the size, shape, or other characteristics of the fluid channel in the needle sled to control the time or rate of medication delivery.

FIG. 9A shows an exploded view of two halves of the channel, and FIG. 9B shows these two halves together to form the curved channel.

FIG. 10A shows an exploded view of the medication pouch with the cap assembly removed to show a fluid channel covered by a dual septum. FIG. 10B shows a side section view of the pouch needle piercing the dual septum from the side and of a fill needle piercing the dual septum from the bottom.

FIG. 12A shows an exploded view from the top, and FIG. 12B shows a view from the bottom to show how the push carriage locks into the needle sled.

FIG. 14 shows an architectural block diagram showing selected components of an illustrative patch and relationships among the components.

DETAILED DESCRIPTION OF THE INVENTION

A mechanically driven medication delivery patch will now be described. In the following description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

FIGS. 1A, 1B, and 1C show top and bottom views of an illustrative embodiment of the medication delivery patch 100. The patch contains an internal pouch (not visible) between the top cover and the bottom surface that may be filled with a medication or other fluid. One or more embodiments may use the patch for delivery of any type of drug, nutrient, medical fluid, vitamin, supplement, nutraceutical, or any other fluid or gel or solution to the body of a user. The characteristic of the fluid includes aqueous, oily, emulsions, micro or nano suspensions, gels depending on needle gauge wherein the fluid includes a wide viscosity range 0.5 centipoise to 200 centipoise. The user may be for example a human or an animal. The embodiment 100 is entirely mechanically driven: it contains no electronics or electrical parts and requires no source of electrical power. Most of the components of patch 100 are not visible in FIGS. 1A, 1B, and 1C; these components are illustrated in other figures and described below.

Figure 1:
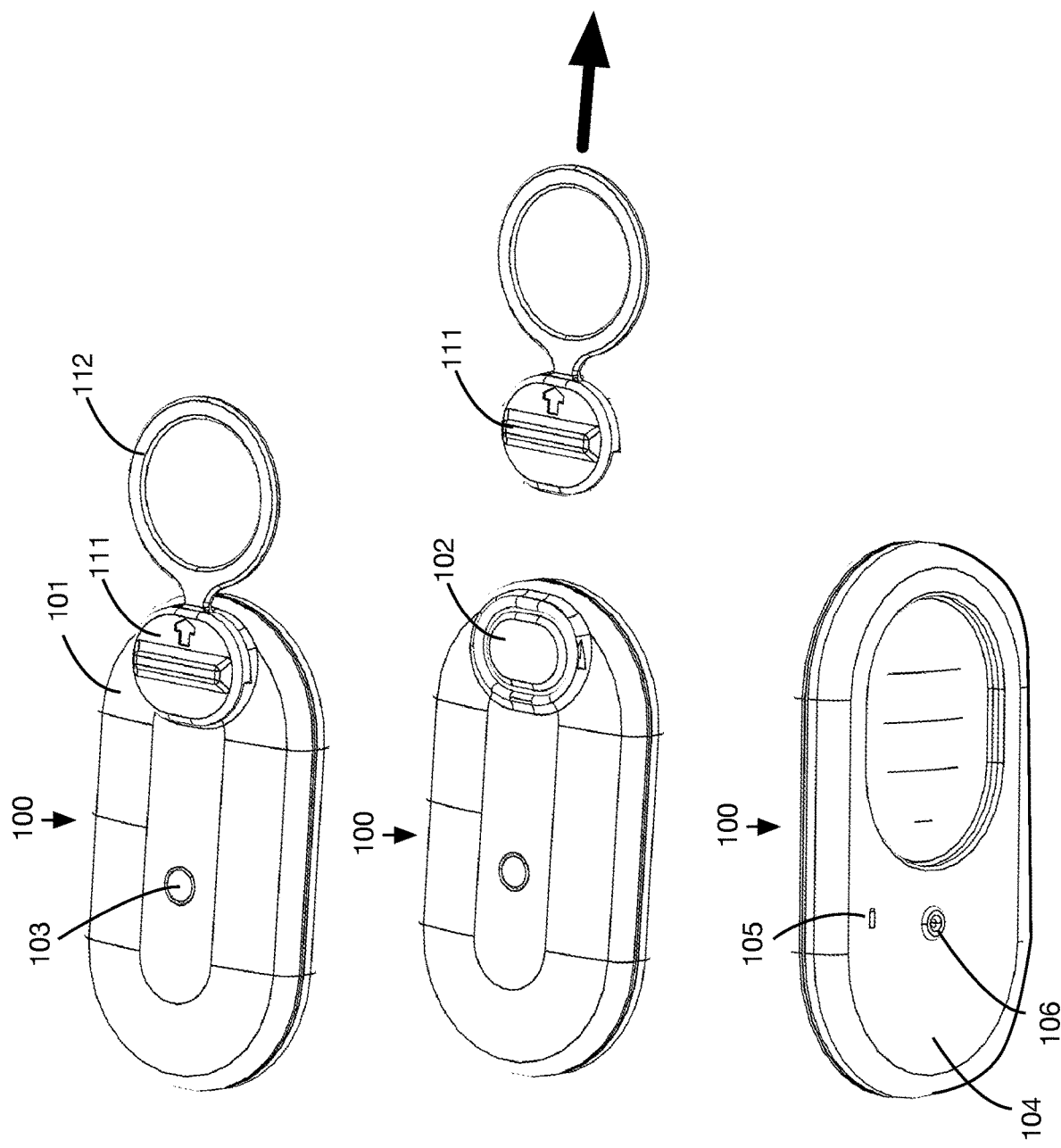
FIG. 1A shows a top view of an embodiment of a mechanically driven medication delivery patch prior to use.
FIG. 1B shows the embodiment of FIG. 1A with the safety cover removed to show the activation button.
FIG. 1C shows a bottom view of the embodiment of FIG. 1B.

The top side of 100 shown in FIG. 1A illustrates a top cover 101, with an activation button on the top side that is initially covered with a safety cover 111. (The activation button 102 is shown in FIG. 1). The safety cover 111 prevents a user from accidentally pressing the activation button. A pull ring 112 (or similar element) may be connected to safety cover 111. To use the patch, a user (or someone assisting the user) may first remove safety cover 111 to expose activation button 102, as shown in FIG. 1B; this person may then start the delivery of the patch contents by pressing the activation button 102. As described below, pressing this button initiates a chain of events that result in the pressurization of the medication pouch, the puncturing of the pouch septum, the emergence of a needle from the bottom of the pouch, and flow of the contained fluid into the user. The embodiment 100 also has one or more clear windows 103 in the top cover 100 that will display an indicator when the delivery of the patch contents is complete, and the needle has been retracted from the user. The activation button 102 is accessible through top cover 101. In one or more embodiments an activation button or a similar activation input may be located anywhere on the patch that is accessible to the user. The button area is sealed to the outside to prevent ingress of liquid or microbes. There may be for example a seal around the button and an elastomeric coating covering all connecting points of the different pieces. One or more embodiments of the invention include a secure seal between top cover 101 and bottom surface 104 to maintain the sterility of the needles held within.

FIG. 1C shows the bottom side of patch 100. The bottom surface 104 of the patch may for example be placed against the skin of the user or coupled to the user's body in some manner. This surface may be adhesive for example; it may be covered by a protective film or other covering surface that is first removed before the patch is applied to the skin. The strength of the adhesive may be selected based on the expected length of time the patch will be applied to the skin; a longer duration delivery may require a stronger adhesive. Bottom surface 104 has an indentation 105 through which the needle emerges to pierce the skin, as described below. The bottom surface also has a port 106 through which the patch may be filled, as described below. These holes 105 and 106 may be covered with a film to ensure that the internal region of the patch is sealed. The needle that emerges to pierce the skin may pierce this film as it exits the patch through hole 105, and a needle for filling may pierce the film to enter the interior of the patch through hole 106. One or more embodiments enable a duration of delivery between 5 seconds and 7 days. Embodiments of the invention deliver medications that include bioactive molecules or substances, peptides, proteins, small molecules, vaccines, vitamins, minerals, biocompatible fluids.

Figure 2:
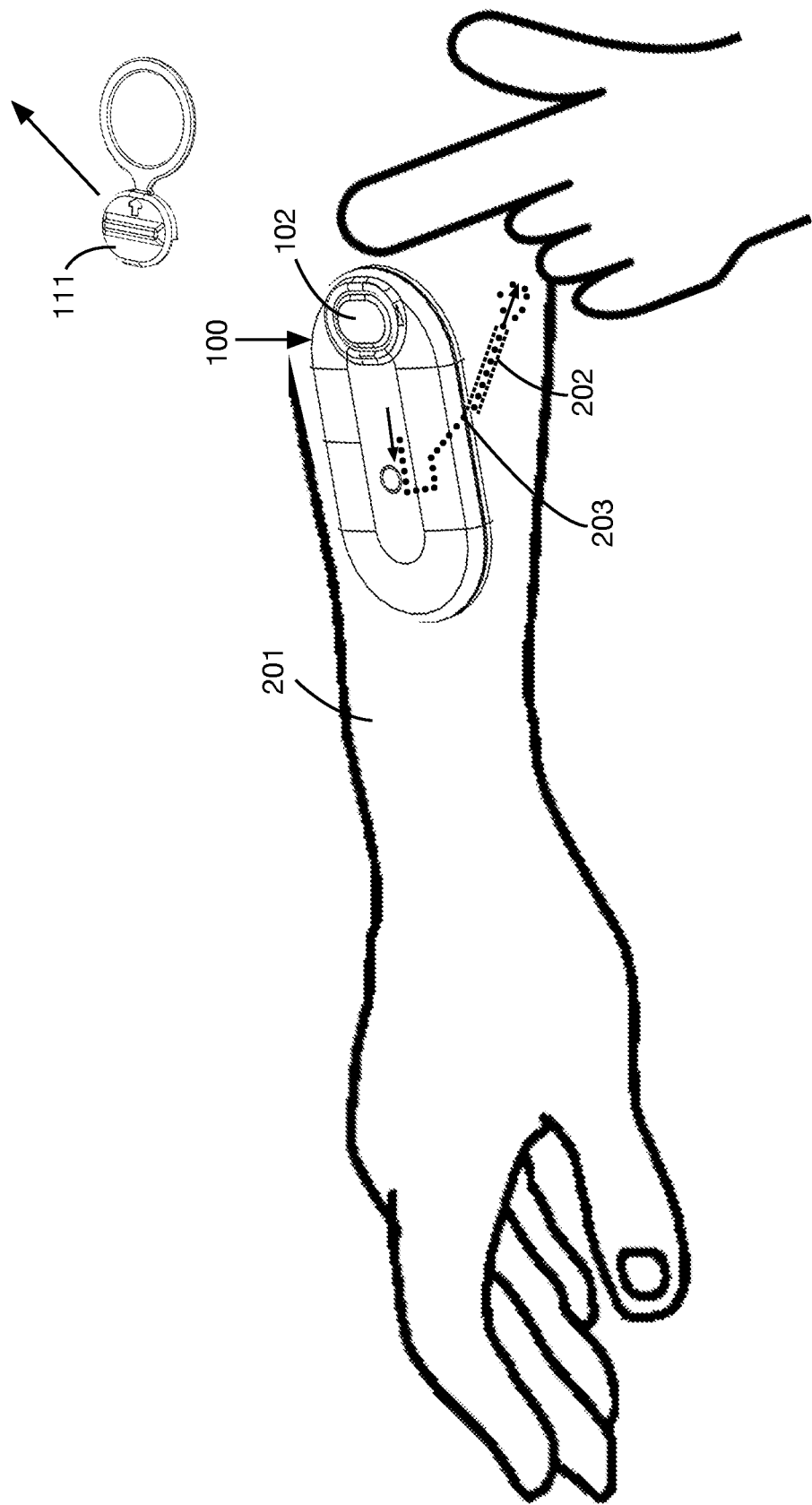
FIG. 2 shows illustrative use of the embodiment shown in FIGS. 1A and 1B: the patch is placed on a user's skin, the safety cover is removed, and an activation button is pressed to start delivery of the medication in the patch to or through the skin of the user.

FIG. 2 shows an illustrative use case for the patch 100. A protective film or surface covering the bottom surface of the patch may be first removed, for example to expose an adhesive surface that sticks to the skin. A user or caregiver then places the patch 100 on the skin 201, which may be anywhere on the body. One or more embodiments may be utilized on the abdomen, thighs and arm or forearm as shown. FIG. 2 shows placement on an arm; one or more embodiments may be configured for example to be placed on the front abdomen, or any other portion of the body that facilitates delivery of the medication enclosed in the patch. The user or caregiver then removes the protective cover 111 and presses the activation button 102, which sets in motion a chain of events that results in a skin needle 202 protruding from the bottom surface of the patch and piercing the skin 201, and results in a flow of the fluid 203 contained in the patch from the pouch in the patch through the skin needle 202 and into the user. Fluid 203 may be any medication or other solution or gel or fluid that is to be delivered to or through the skin of the user.

We now describe illustrative internal components of one or more embodiments of the invention, and the events and actions that cause delivery of the fluid and then retraction of the needles when delivery is complete. In the embodiments shown, all components and linkages are mechanically driven, for example using stored mechanical energy in springs or similar energy storage devices. These embodiments have no electrical or electronic components, so may lower cost, improve reliability, and may make the patch more robust. One or more embodiments may modify these components and linkages as desired to achieve the same effects of fluid delivery upon activation, followed by needle retraction when delivery is complete.

Figure 3:
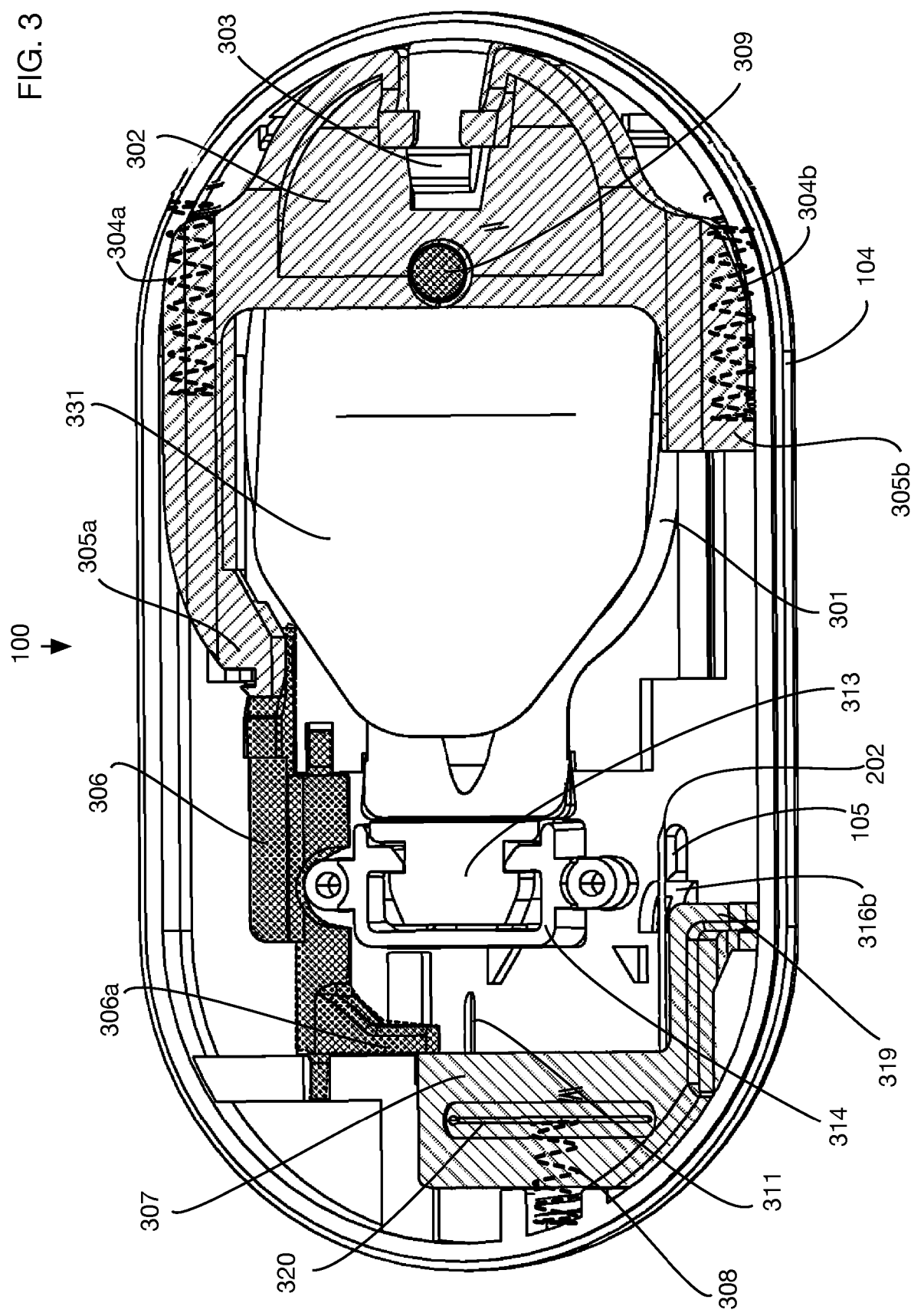
FIG. 3 shows the embodiment of FIG. 1A with the top cover and activation button removed to show the internal components.

FIG. 3 shows patch 100 with the top cover and activation button removed. The internal components are shown in their state before activation. (Some internal components are largely or completely hidden in this view.) A pouch 301, which may be made of a flexible or compressible material, contains the fluid to be delivered. This pouch may be of compatible size, shape, and material. One or more embodiments of pouch 301 may enable a volume of fluid between 0.3 to 50 mL. The pouch can withstand up to 82 psi in one or more embodiments, while typical pressure within the pouch when filled may be 2 to 7 psi for aqueous fluids. A plate 331 may lie on top of the pouch. A wedge 302, which starts at an initial position at the edge of the pouch, is forced against the plate after activation, in this embodiment by wedge springs 304*a* and 304*b*, or by a similar wedge force element, applying pressure to the fluid contained in the pouch to cause delivery of the fluid through the needles described below. (In the view of FIG. 3, the springs are largely below the wedge, so they are shown in dotted lines.) The wedge 302 is shown in FIG. 3 with diagonal hatching for clarity. Wedge 302 includes integral or attached "arms" 305*a* and 305*b* that extend towards the left side (in FIG. 3) of the patch; these arms move with the wedge and they activate or retract other components as described below. Prior to activation, the wedge 302 is held in its initial position by a wedge latch 303; this latch is released when the activation button is pressed. Embodiments of pouch 301 may be made from biocompatible polymers or polymer laminates or blends of polymers with one or more embodiments providing a clear flexible wall for the pouch. These polymers utilized for pouch 301 include commonly used polymers for injectable products, such as, but not limited to polyethylene, polypropylene, COP, COC, PCTFE, EVOH, polyurethane.

When the wedge 302 starts moving, the arm 305*a* of the wedge (or a similar element integrated into or coupled to the wedge) initially moves forward a slight amount to allow rotation which then rotates a pivoting sled release element 306 (shown cross-hatched in FIG. 3) to release latch 306*a* that holds in place a needle sled 307. This needle sled may be any type of element or elements that move needles to cause delivery of the fluid in the pouch to the user. For clarity the needle sled 307 is shown in FIG. 3 with diagonal hatching. After the release of latch 306*a* the needle sled 307 is driven forward by a spring 308, or similar needle sled force element, moving it from the retracted position (as shown in FIG. 3) to a deployed position to deliver the fluid to the user. The illustrative needle sled 307 contains or is coupled to two needles. Skin needle 202 will exit the bottom of the patch through hole 105 to pierce the user's skin. Pouch needle 311 will enter a fluid channel coupled to the pouch through a cap assembly 313, to allow the fluid in the pouch to flow from the pouch into the pouch needle. Needle sled 307 also has a fluid channel 320 that connects the interior of the pouch needle 311 to the interior of the skin needle 202 to complete the fluid flow path from the pouch into the user. The channel 320 may be covered by a hydrophobic membrane that allows air to vent to atmosphere at the beginning of the delivery cycle. When the vent is fully wetted it seals against the fluid completing the fluid pathway. The skin needle 202 may be deflected through a curved channel or similar feature so that it enters the skin at an angle when it protrudes from the bottom of the patch (through a film that seals the hole); FIG. 3 shows a bottom portion 316*b* of a needle guide element with this curved channel. Initially, when retracted, the skin needle 202 may be for example roughly horizontal (roughly parallel to the user's skin when the patch is applied).

Illustrative gauges for the pouch needle 311 in one or more embodiments may be for example in the range of 18 gauge to 27 gauge; illustrative gauges for the skin needle 202 may be for example in range of 25 gauge to 34 gauge. The skin needle 202 may have varying lengths in various embodiments, to achieve the desired depth of entry into the skin or through the skin. For intradermal injections, illustrative skin needle lengths may be for example in the range of 3 mm to 5 mm; for subcutaneous injections, illustrative skin needle lengths may be for example in the range of 12 mm to 16 mm. The angle of insertion for intradermal injections may be between 5 and 15 degrees inclusive, while the angle of insertion for subcutaneous insertion may be 45 to 90 degrees in one or more embodiments.

After delivery of the fluid in the pouch to the user is complete, the skin needle 202 may be retracted from the user into the interior of the patch (for safety and to facilitate patch removal), and the pouch needle 311 may be retracted from the septum covering the fluid channel connected to the pouch (for example to prevent any residual fluid from leaking and to ensure delivery of a precise amount of the fluid to the user). In embodiment 100, these needle retractions are achieved by pushing the needle sled 307 backwards (towards its retracted position) when delivery is complete. The pushing of the needle sled backwards may be performed by the wedge arm 305*b*, which contacts corresponding arm 319 of the needle sled when the sled is deployed and the wedge has moved across the plate 331 to an end-of-delivery position where medication delivery stops and needle retraction begins. Motion of the wedge 302 therefore may provide multiple functions of releasing needle sled latch 306*a* upon activation, forcing the fluid out of pouch 301 for delivery, and retracting the needle sled 320 (and the needles 311 and 202) after delivery.

A delivery complete indicator 309 is integrated into or attached to wedge 302. When the wedge is at the end-of-travel position, where it is at the limit of its motion (leftwards in FIG. 3), this indicator is positioned directly below the window 103 in the top cover. Appearance of this indicator in the window shows the user that the delivery is complete and the needles are retracted, and that the patch can be removed. The indicator may for example be of a distinctive color (such as red or yellow), shape, or pattern for easy recognition. One or more embodiments may put one or more visible indicators in any area of the patch, including but not limited to the top of the patch cover. For example, an indicator may be visible through a side of the patch rather than (or in addition to) through the top cover. In one or more embodiments, one or more indicators may show the progress of medication delivery in addition to an indication that the process is complete, for example along the side of one or more embodiments of medication delivery patch 100.

Figure 4A:
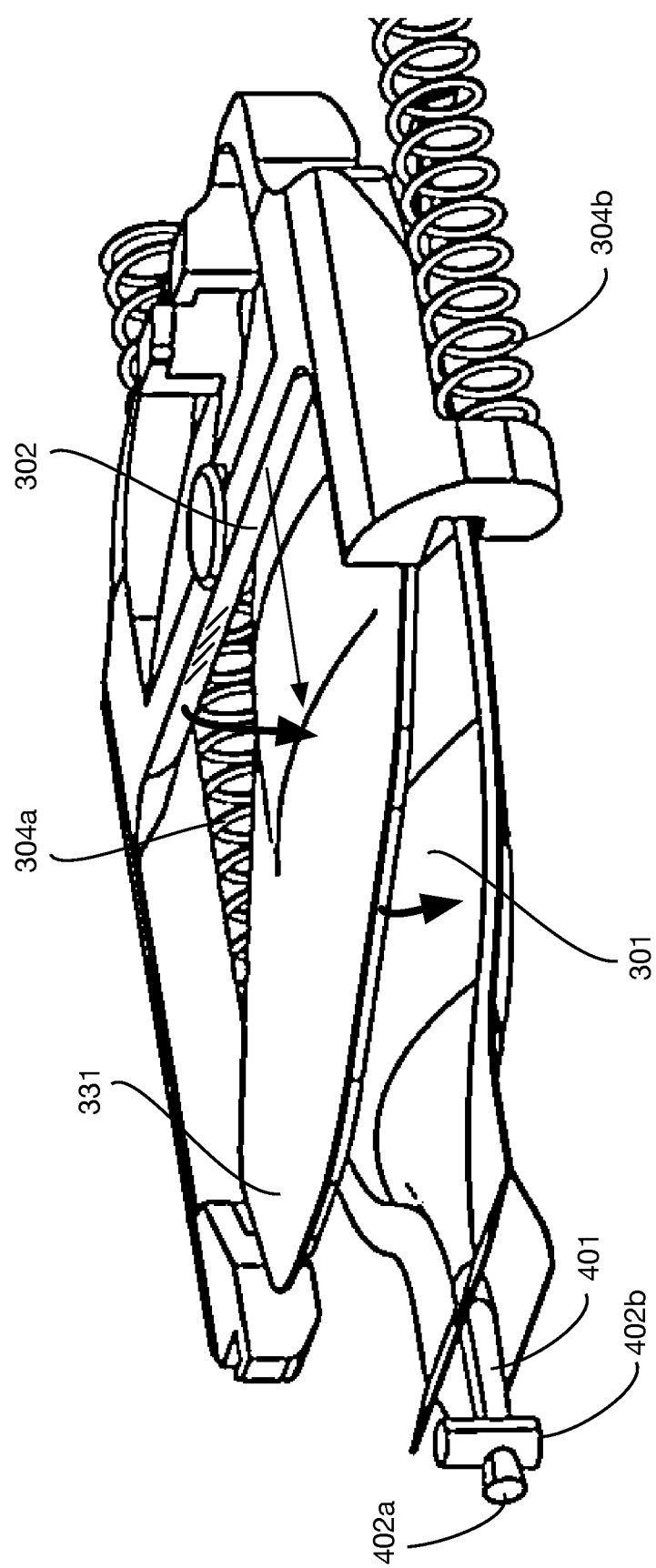
FIG. 4A shows the filled medication pouch of the embodiment of FIG. 1, with a wedge that presses on a plate to apply pressure to the pouch as the wedge moves along the plate.

FIG. 4A shows a view of the wedge 302, the plate 331, and the pouch 301. A port 401 is attached to an opening in pouch 301; this port has dual openings 402*a* (for the pouch needle) and 402*b* (for filling) as described below. As springs 304*a* and 304*b* force the wedge forward, the sloped surface of the wedge 302 presses downward on plate 331, which in turn presses on pouch 301. The plate, and the wedge surface or surfaces that contact the plate may be of any compatible size and shape. In one or more embodiments, the wedge or similar element may push directly on the pouch, rather than on a plate that in turn presses on the pouch. In one or more embodiments the wedge or other element that applies pressure may travel along any surface of the pouch, including the top, bottom, or side of the pouch. In one or more embodiments, the wedge may not travel across the pouch, but instead may push against any surface of the patch to apply pressure; for example, the wedge may be forced against the top or bottom surface of the pouch when it is released. The plate may have a compressible foam or membrane between it and the pouch to aide in fully evacuating the pouch.

Figure 4B:
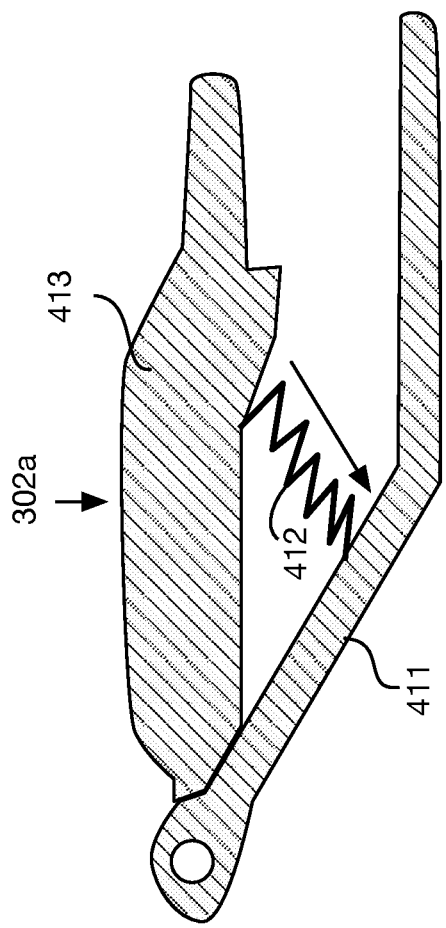
FIGS. 4B and 4C show side views of two other embodiments of a wedge.
Figure 4C:
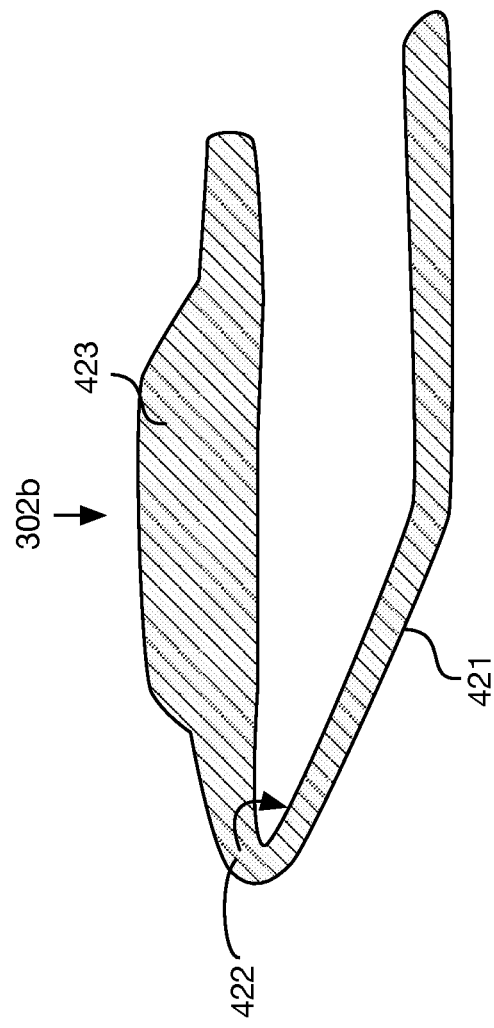

In one or more embodiments of the invention, force generating element(s) may be integrated into the wedge element; side views of illustrative examples are shown in FIGS. 4B and 4C. In the wedge embodiment 302*a* shown in FIG. 4B, the wedge has a lower section 411 that presses on the pouch; this section 411 is coupled to an upper wedge section 413 by a spring or similar force element 412.

Sections 411 and 413 may be coupled by a pivot joint for example. In embodiment 302b shown in FIG. 4C, the force of spring 412 is replaced by resistance of a portion 422 of the wedge that joins the upper section 423 and lower section 421; for example, this portion 422 may be made of a flexible but relatively stiff material.

Figure 5:
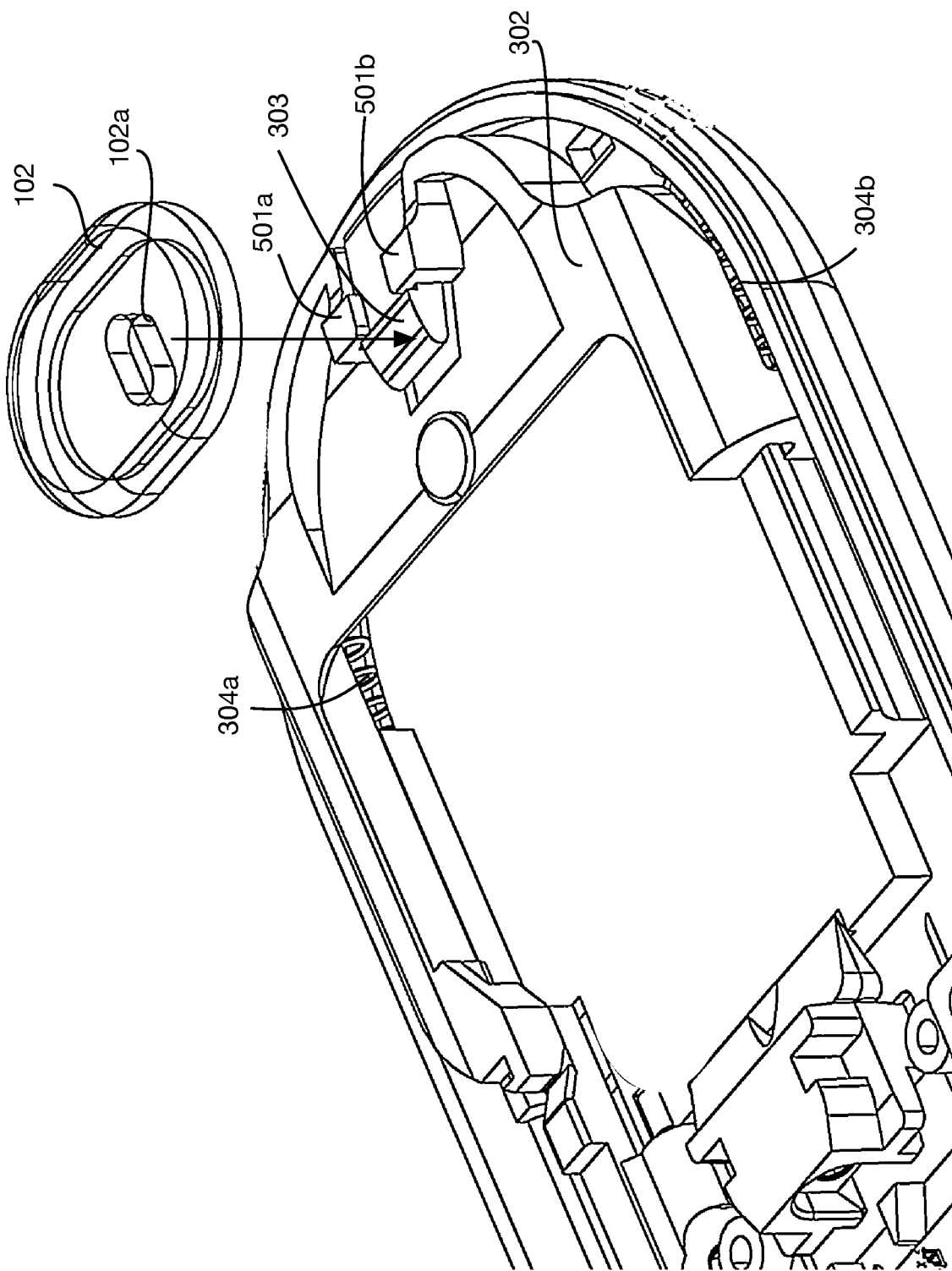
FIG. 5 shows a closeup view of the activation button, the wedge latch that holds the wedge in place prior to activation, and the wedge force elements that push the wedge across the medication pouch.

FIG. 5 shows an illustrative mechanism for activating the delivery of fluid from the pouch. Activation button 102 is shown in an exploded view above the patch case and is shown as a wireframe to illustrate its internal shape. Latch 303 holds portions 501a and 501b of wedge 302 in place prior to activation, resisting the movement of the wedge. When button 102 is pushed down, protrusion 102a below the button presses down on latch 303 and these the portions 501a and 501b can move over the top of the latch, releasing the wedge to move forward from the force provided by springs 304a and 304b. One or more embodiments may couple the activation button or similar activation element to the wedge latch or latches in any desired manner. The button may have one or more protrusions or extensions that contact or otherwise release any latch or latches. The activation button protrudes through the top cover of the patch and may be surrounded by a seal (such as a silicone gasket) that seals the gap around the edge of the button between the button and the top cover. These features may be configured to require sufficient force for activation such that the device will not accidentally fire due to shock or vibration.

When wedge 302 moves forward after activation, it first moves to unlock the rotating release mechanism and then forces 306 to rotate thereby releasing the needle sled 307 so that the attached needles can pierce the skin and the pouch septum to initiate delivery of fluid to the user. FIGS. 6A, 6B, and 6C show an illustrative mechanism for release of the needle sled. FIGS. 6A and 6B show the needle sled 307 prior to activation. The needle sled is held in place by a needle sled latch 306a that is coupled to pivoting needle sled release element 306. This sled release element 306 acts as a linkage between the arm 305a of the wedge and the latch 306a. This release element 306 is shown cross-hatched in FIGS. 6A through 6C for clarity. Needle sled release element 306 is constrained to move only by pivoting around its longitudinal axis. FIG. 6B shows a cylindrical extension 306b at one end of element 306, which fits into a corresponding cylindrical pocket; a similar feature is on the other end of element 306. These two cylindrical extensions support the release element 306 and allow it to rotate. Latch 306a initially covers a part of the front face of needle sled 307, preventing the needle sled from moving forward. This portion of the needle sled that contacts the latch 306a is not visible in FIGS. 6A and 6B, but is visible as region 307a in FIG. 6C where the needle sled release element 306 has rotated to release the needle sled. FIG. 6B shows that the needle sled release element 306 is locked to the wedge arm 305a in region 601, which prevents the release element 306 from rotating prior to activation. This locking prevents the needle sled from being unlatched accidentally due to shock or vibration. When the wedge is released by the activation button, it moves forward so that the needle sled release element 306 is no longer locked to the wedge arm. The tip of wedge arm 305a presses on the corresponding tip of the release element 306, causing it to rotate and raise latch 306a, as shown in FIG. 6C; this allows the needle sled to move forward.

The pivoting release mechanism shown in FIGS. 6A through 6C is an illustrative mechanism to release the needle sled as a result of the forward motion of the wedge. One or more embodiments may use other types of linkages and latches to link the wedge motion to the release of the needle sled. In one or more embodiments the activation button or similar activation input may directly release a needle sled latch, instead of using the wedge motion to release the needle sled latch.

Figure 7B:
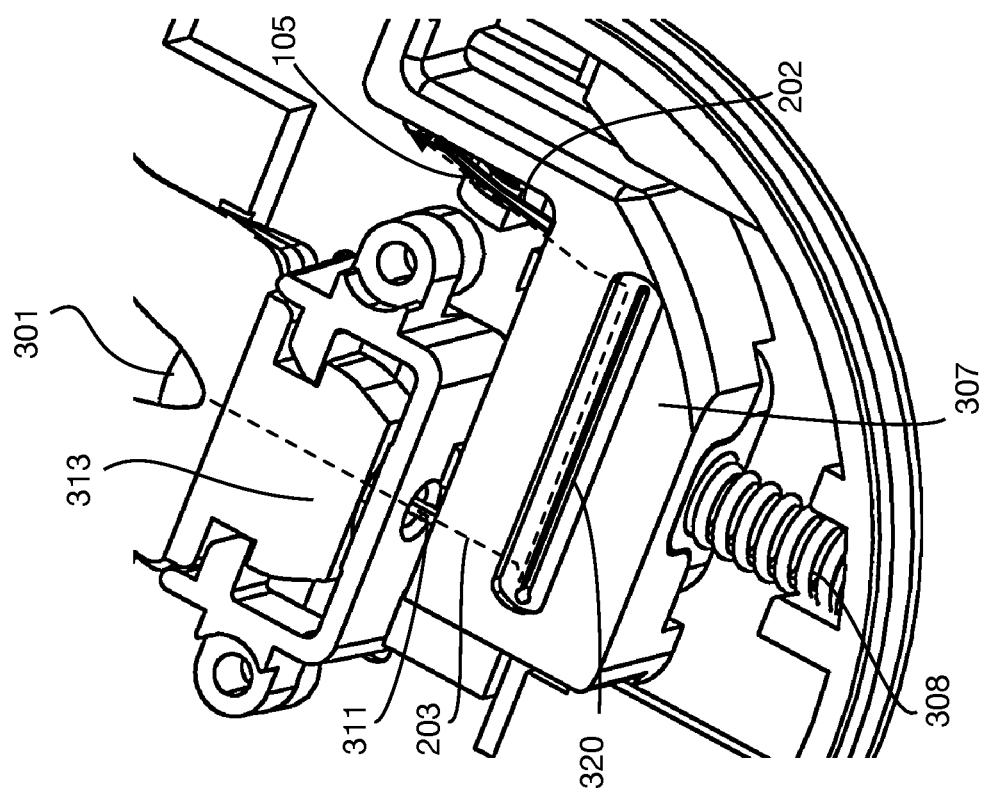
FIG. 7B shows the needle sled in its deployed position, with the pouch needle connected to the pouch and the skin needle deflected downwards through the bottom of the patch and into the user's skin.
Figure 7A:
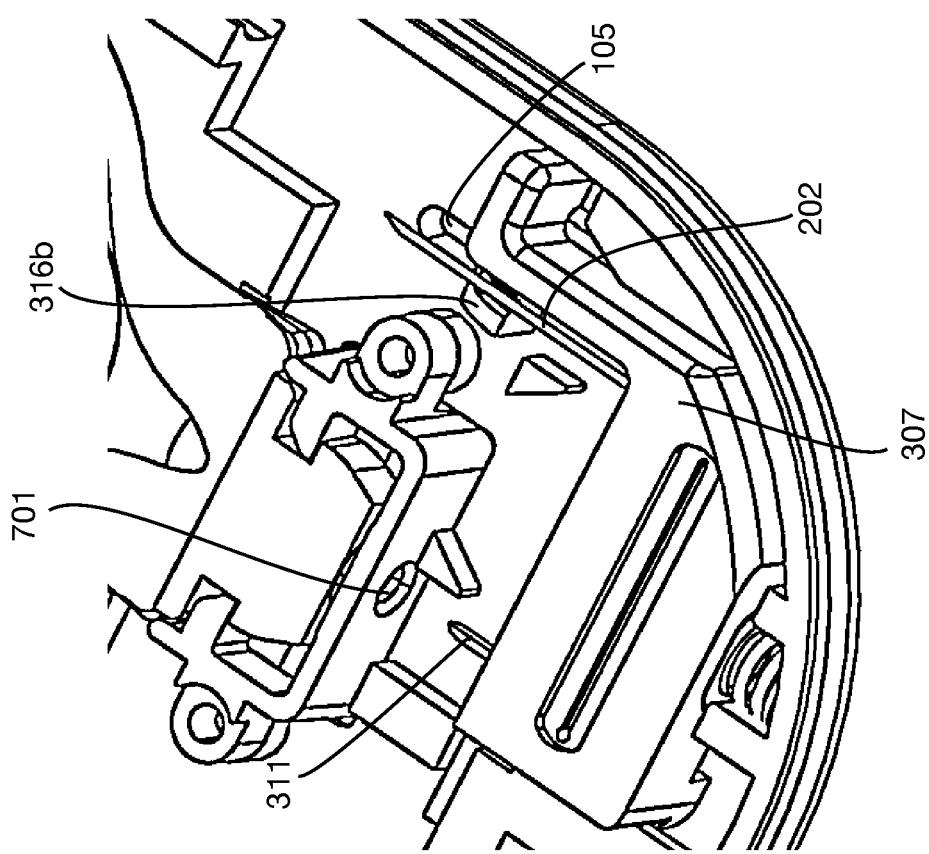
FIG. 7A shows an illustrative needle sled prior to activation, in its retracted position.

FIGS. 7A and 7B show needle sled 307 before and after it has moved forward to insert needles, respectively. In FIG. 7A, with the needle sled in its retracted position before activation, pouch needle 311 is positioned opposite a conduit or aperture 701 that leads to a septum covering the fluid pouch fluid path, and skin needle 202 is positioned near hole 105 in the bottom of the patch case. FIG. 7B shows sled 307 after it moves forward to its deployed position under the force from needle sled spring 308. Pouch needle 311 has pierced the septum covering the pouch fluid path. The skin needle 202 is deflected downwards through hole 105 and through a film covering the hole and it enters the skin. Fluid 203 then flows from the pouch 301 to the pouch needle 311, through the fluid channel 320 in the needle sled, through the skin needle 202, and into the user.

In one or more embodiments of the invention, one or more components of the patch may be configured or selected to control the rate of fluid delivery or the total time of fluid delivery (or both). Time of delivery may be measured for example between a start time when the activation button is pressed, and an end time when the wedge reaches its end-of-travel position. This feature allows the patch to be configured for different medications and use cases, or to adapt to different patient needs or prescriptions. One component that may be used to control the rate or time of delivery is the fluid channel 320 in the needle sled 307 that connects the pouch needle 311 and the skin needle 202. The diameter, length, shape, materials, valves, flow restrictors, or other features of this fluid channel may be modified to affect delivery speed and time. This channel may for example include a microfluidic channel. In one or more embodiments the features of the channel may include valves or flow restrictors to modify the rate of flow through the channel. For example, FIG. 8A shows an illustrative embodiment with a fluid channel 320a that is selected for rapid delivery time 801a. FIG. 8B shows an illustrative embodiment with a fluid channel 320b that is selected for much longer delivery time 801b. Channel 320b may for example be longer, narrower, and it may contain one or more valves or flow restrictors 802 that affect the flow rate through the channel. Illustrative fluid delivery times in one or more embodiments may range for example from 10 seconds to 7 days.

Figure 9B:
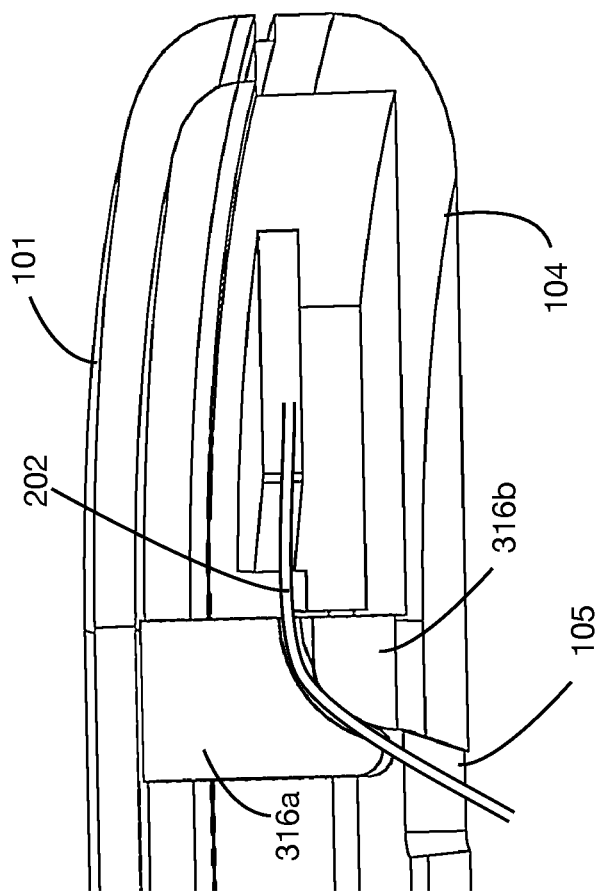
FIGS. 9A and 9B show a curved channel that deflects the skin needle so that it exits the bottom of the patch and enters the skin at an angle.
Figure 9A:
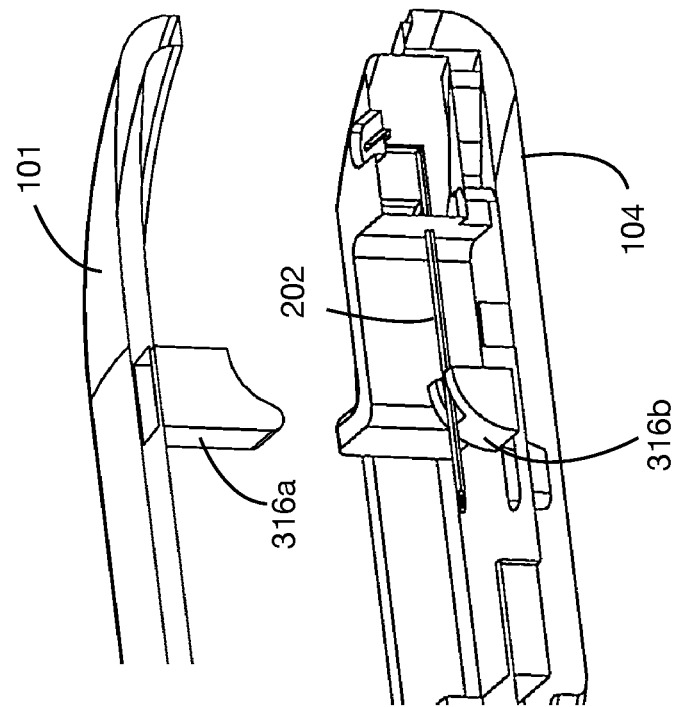

FIGS. 9A and 9B illustrate a curved channel that deflects skin needle 202 downwards so that it passes through the bottom cover of the patch and enters the user's skin at an angle. FIG. 9A shows a cutaway view of one half of the top cover 101 and a corresponding half of the bottom cover 104; these parts are shown exploded from one another. Integrated into or coupled to the bottom cover is the bottom portion 316b of a needle guide element with a curved upper surface, and integrated into or coupled to the top cover is the corresponding top portion 316a of the needle guide element with a mating curved surface. In this illustrative embodiment, the curved needle channel is formed between these two elements 316a and 316b. FIG. 9B shows a cutaway view through the center of the joined elements 316a and 316b, showing the curved channel formed between these elements through which skin needle 202 passes and is deflected through hole 105 in the bottom housing 104. One or more embodiments may use any element or combination of elements to deflect or guide the skin needle through any channel or aperture to exit the patch and to enter the user's skin. The deflection amount of the skin needle may be varied in various embodiments; typical values for the angle at which the skin needle enters the skin may be for example between 30 degrees and 90 degrees.

FIG. 10A shows an exploded view of pouch 301 elevated from the bottom housing 104, with the cap assembly 313 removed to show a dual septum 1001 that covers the ports 402a and 402b into the fluid conduit 401 connected to the pouch. Cap 313 holds dual septum 1001 in place when it is installed. The dual septum contains two different regions that we refer to as the pouch septum and the fill septum. The side-facing portion of dual septum 1001 is the pouch septum 1001a that is across from pouch needle 311; the pouch needle 311 pierces this pouch septum portion 1001a of the dual septum 1001 when the needle sled moves forward. The bottom portion of dual septum 1001 is the fill septum 1001b that is above fill hole 106 in the bottom housing 104; this fill septum may be used for filling the pouch. FIG. 10B shows a side view of pouch 301 and dual septum 1001. A pharmacist or other supplier may pierce the fill septum with a syringe 1002 or similar filling device inserted through hole 106 to fill the pouch 301 with fluid before delivering it to the user. This feature may allow providers to stock embodiments of the invention and then fill them with desired fluids on demand. In one or more embodiments, a fill port may not be provided and the pouch 301 may be prefilled; for example the pouch may be factory filled during patch assembly. If the pouch is pre-filled, fill septum 1001b and fill hole 106 may not be included in one or more embodiments.

Figure 11A:
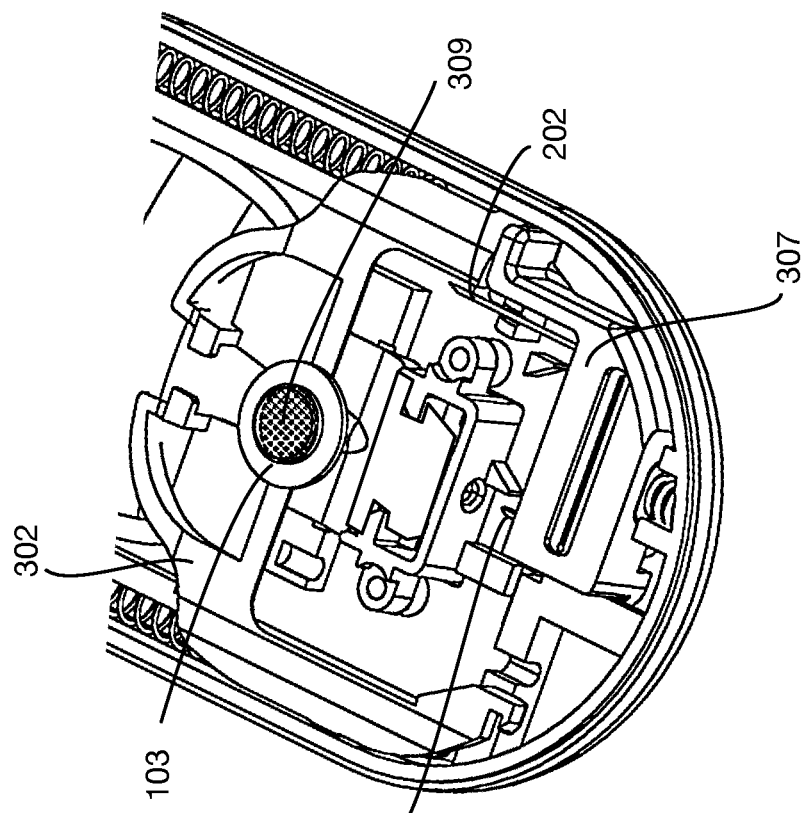
FIG. 11A illustrates the wedge at its end-of-delivery position where it begins to push the needle sled backwards.
Figure 11B:
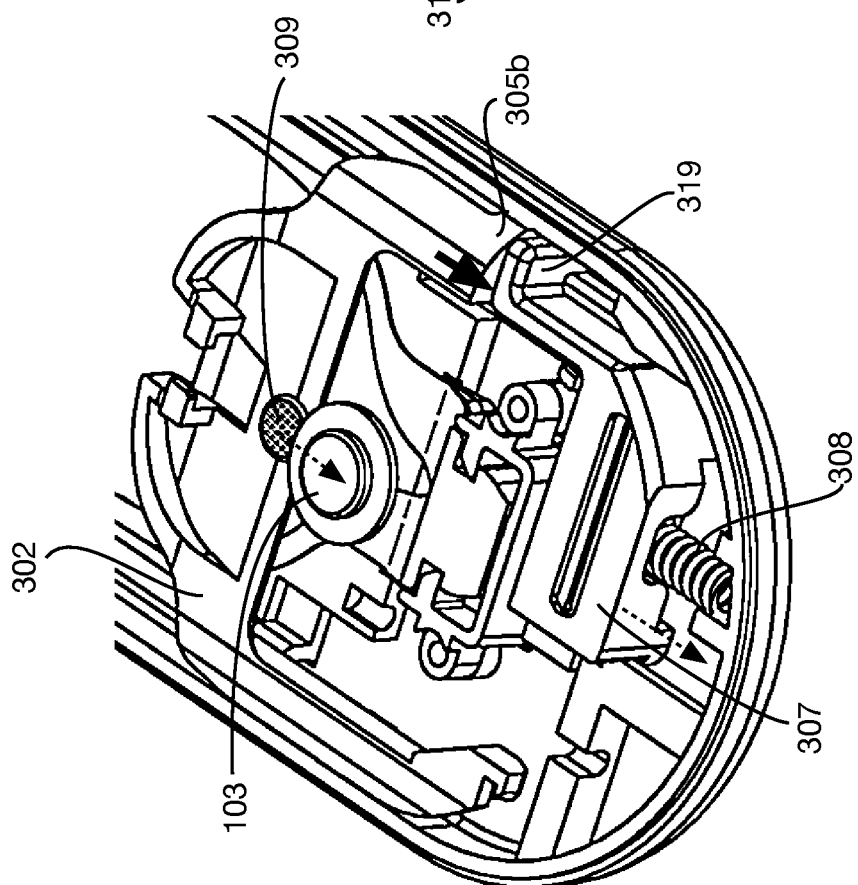
FIG. 11B shows the needle sled fully retracted when the wedge reaches its end-of-travel position.

After delivery of the desired amount of fluid in the pouch to the user, one or more embodiments of the patch may retract the needles from the skin and the pouch to stop fluid flow and allow the user to remove the patch. FIGS. 11A and 11B illustrate a method that may be used to retract the needles in one or more embodiments. FIG. 11A shows needle sled 307 in the deployed position, with the skin needle and pouch needle in the user's skin and in the pouch septum, respectively. When wedge 302 completes its travel across the plate and arrives at its end-of-delivery position (as shown in FIG. 11A), wedge arm 305b contacts corresponding arm 319 of needle sled 307. As shown in FIG. 11B, the wedge continues to travel forward to its end-of-travel position and pushes the needle sled 307 back towards its initial (retracted) position, retracting the needles 311 and 202. FIG. 11A also shows indicator 309 on the wedge and window 103 of the top cover. As the wedge moves forward to the end-of-travel position shown in FIG. 11n, the indicator 309 on the wedge reaches its final position under the window 103, indicating to the user that the process is complete, and the patch can be removed.

Figure 12B:
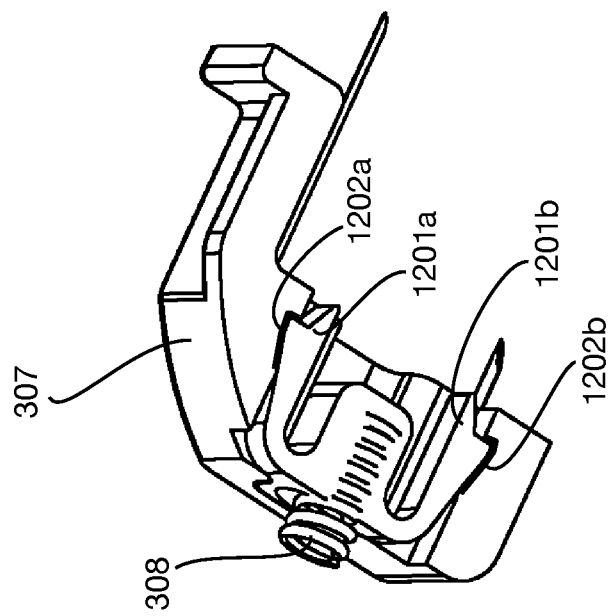
FIGS. 12A and 12B show an illustrative embodiment with a needle sled push carriage that pushes the needle sled forward and then decouples from the needle sled.
Figure 12A:
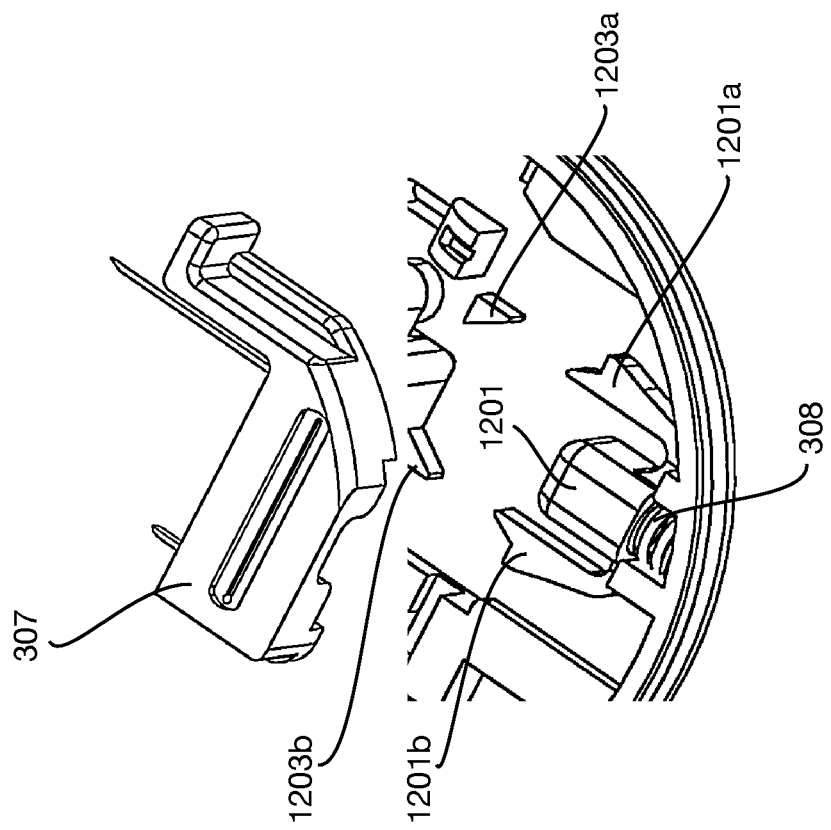
Figure 13:
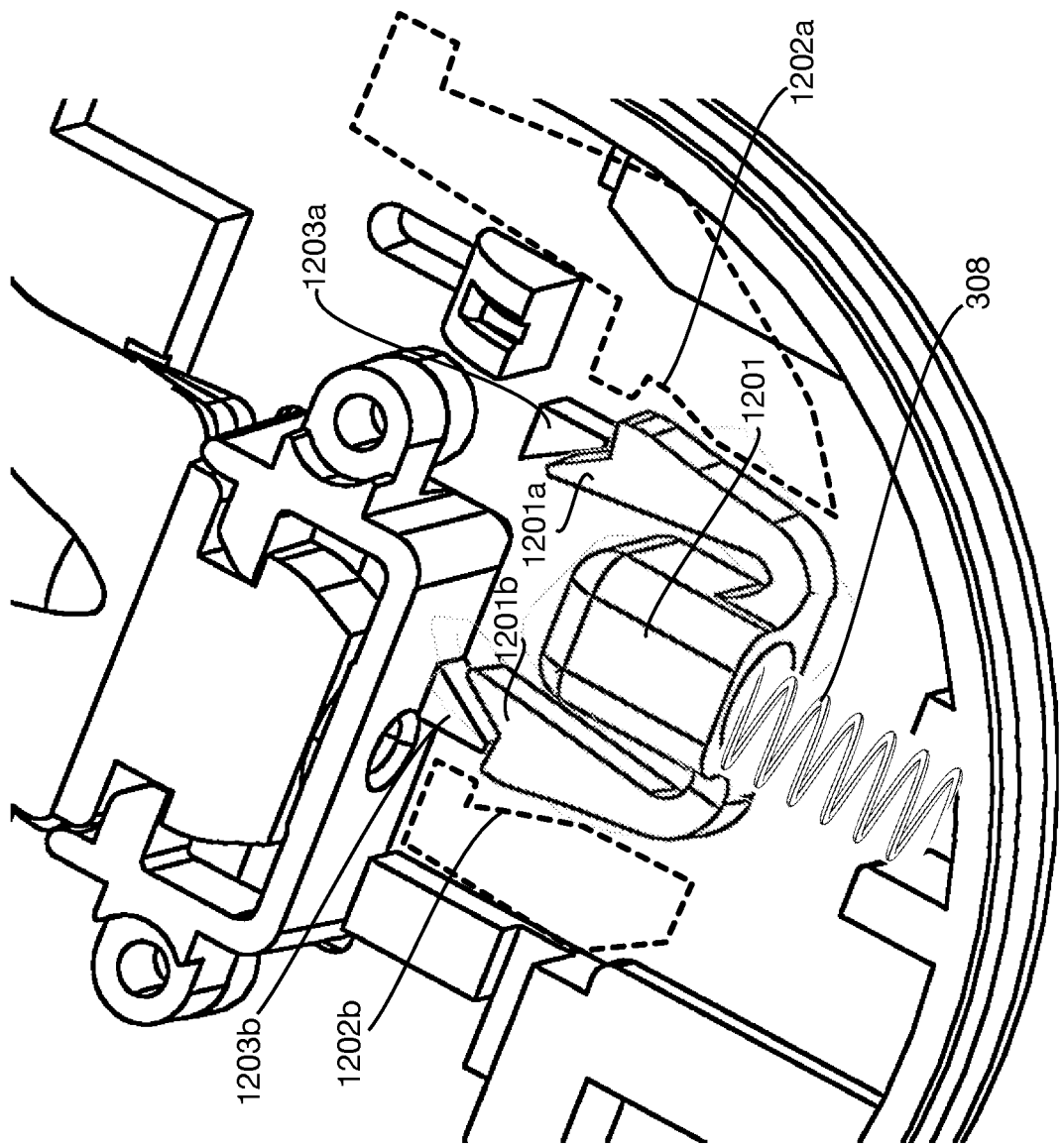
FIG. 13 illustrates how the push carriage embodiment of FIGS. 12A and 12B unlocks from the needle sled when the needle sled is deployed.

One or more embodiments of the invention may incorporate a mechanism to decouple the needle sled 307 from the needle sled spring 308 (or similar force element) after the needle sled is deployed. This decoupling may facilitate the retraction of the needle sled using the force applied by the wedge, as shown in FIGS. 11A and 11B. Although the wedge springs may be selected to be sufficiently strong to overcome the force of the needle sled spring, decoupling the needle sled spring may reduce size, weight, and cost by reducing the size and strength required from the wedge springs. FIGS. 12A, 12B, and 13 show an illustrative mechanism that may be used to provide this needle sled spring decoupling in one or more embodiments. In this illustrative mechanism, the needle sled is not pushed directly by the needle sled spring; instead, as shown in FIG. 12A in an exploded view and in FIG. 12B as an integrated view from below, the needle sled spring is coupled to a needle sled push carriage 1201. This push carriage 1201 is in turn detachably latched into needle sled 307. Push carriage 1201 has flexible arms 1201a and 1201b with protrusions that fit into mating indentations 1202a and 1202b in the needle sled, as shown in the view from below in FIG. 12B. When push carriage 1201 is latched into the needle sled 307, the force from spring 308 is transmitted to the needle sled, moving the needle sled forward to its deployed position. As shown in FIG. 12A, integrated into or coupled to the bottom housing of the patch are two sloped carriage release elements 1203a and 1203b. These sloped elements press against arms 1201a and 1201b when the push carriage 1201 reaches the end of its forward travel. The arms 1201a and 1201b are then pinched inward, releasing them from the indentations 1202a and 1202b on the needle sled, and thereby unlatching the needle sled from the push carriage. This action is shown in FIG. 13, which shows push carriage 1201 in its deployed (fully forward position). The ends of the needle sled are shown in dotted lines to illustrate the position of the indentations 1202a and 1202b; because arms 1201a and 1201b are pinched inwards, the needle sled is decoupled from the push carriage at this point. Therefore, the wedge can push the needle sled backwards, retracting the needles, without having to overcome the force of the needle sled spring 308.

The specific sizes, shapes, and arrangements of the patch components described above are illustrative; one or more embodiments may use other components with different shapes or sizes that are arranged in different configurations. FIG. 14 shows a block diagram view of one or more embodiments of the invention that describes functional relationships among illustrative components that are independent of components' sizes, shapes, positions, and orientations. One or more embodiments of the invention may use a subset of these components; for example, as described above, a release mechanism for a needle sled push carriage may not be needed if the force applied to the wedge is sufficient to overcome the force of the needle sled spring or similar force element.

As shown in FIG. 14, in one or more embodiments an activation input 102, such as a button, lever, switch, or other control, is activated to release a wedge latch 303 that holds a wedge 302 in its initial position. The wedge latch 303 may be any element that applies a force to hold the wedge into position. The wedge 302 may be any element that can apply pressure, either directly or indirectly, to pouch 301 containing the fluid to be delivered. When wedge latch 303 is released, one or more wedge force elements 304 push (or pull or otherwise move) wedge 302. As or shortly after wedge 302 begins to move, it (directly or indirectly) releases a needle sled latch 306a, which holds needle sled 307 in its retracted position. The needle sled force element(s) 308 then push forward the needle sled 307 to its deployed position. In one or more embodiments the needle sled may be pushed forward indirectly via a needle sled push carriage 1201. The needle sled 307 is coupled to or integrated with pouch needle 311 and skin needle 202, and it connects these two needles via a fluid path 320. As the needle sled moves forward to its deployed position, pouch needle 311 connects a fluid path to pouch 301, and skin needle 202 connects this fluid path to the user 201. The skin needle 202 may be deflected by a curved channel 316a and 316b to enter the user's skin at a desired angle. As the wedge moves forward, the applied pressure to the pouch 301 from wedge 302 causes fluid to flow from the pouch 301 through the pouch needle 311, through the path 320 in the needle sled 307, through the skin needle 202, and into user 201. As the wedge reaches an end-of-delivery position, it contacts and pushes backward on needle sled 307, causing retraction of the needles as the needle sled is pushed back to its retracted position. In one or more embodiments with a needle sled push carriage 1201, as the needle sled 307 reaches its deployed position, one or more carriage release elements 1203*a*/1203*b* may release the needle sled push carriage 1201 from the needle sled 307, facilitating retraction of the sled. At the end of its travel, wedge 302 moves delivery complete indicator 309 into view for the user to indicate completion of the fluid delivery and completion of needle retraction.

While the invention herein disclosed has been described by means of specific embodiments and applications thereof, modifications and variations could be made thereto by those skilled in the art without departing from the scope of the invention set forth in the claims.

What is claimed is:

1. A dual needle delivery system that connects and deploys needles of a medication delivery device, comprising:
    a needle sled configured to move between a retracted position and a deployed position;
    a first needle coupled to said needle sled, wherein said first needle is configured to move with said needle sled between said retracted position and said deployed position;
    a second needle coupled to said needle sled, wherein said second needle is configured to move with said needle sled between said retracted position and said deployed position;
    a fluid channel within said needle sled coupling an interior of said first needle and an interior of said second needle;
    wherein
        when the needle sled moves from said retracted position to said deployed position,
            said first needle and said second needle move with said needle sled to said deployed position;
            said first needle receives a fluid to be delivered to a user;
            said second needle penetrates skin of said user; and
            said fluid flows through said first needle, through said fluid channel, and through said second needle into said user;
        when the needle sled moves from said deployed position to said retracted position,
            said first needle and said second needle move with said needle sled to said retracted position;
            said second needle retracts from said skin of said user; and
            said fluid no longer flows through said first needle, and no longer flows through said second needle into said user.

2. The dual needle delivery system that connects and deploys needles of a medication delivery device of claim 1, wherein said medication delivery device is configured to be worn on said skin of said user.

3. The dual needle delivery system that connects and deploys needles of a medication delivery device of claim 1, wherein
    one or more of a shape, length, diameter, materials, valves, and flow restrictors of said fluid channel are configured to provide a desired rate of delivery of said fluid to said user over a desired time period between a start time when said needle sled moves from said retracted position to said deployed position and a finish time when said needle sled moves from said deployed position to said retracted position.

4. The dual needle delivery system that connects and deploys needles of a medication delivery device of claim 3, wherein said fluid channel comprises a microfluidic channel.

5. The dual needle delivery system that connects and deploys needles of a medication delivery device of claim 3, wherein said desired time period is in a range between 10 seconds and 7 days.

6. The dual needle delivery system that connects and deploys needles of a medication delivery device of claim 1, wherein
    a gauge of said first needle is different from a gauge of said second needle.

7. The dual needle delivery system that connects and deploys needles of a medication delivery device of claim 1, wherein
    a gauge of said first needle is in a range between 18 gauge and 27 gauge; and,
    a gauge of said second needle is in a range between 25 gauge and 34 gauge.

8. The dual needle delivery system that connects and deploys needles of a medication delivery device of claim 1, wherein
    said fluid channel is covered by a hydrophobic membrane configured to vent air to atmosphere when said fluid begins to flow through said fluid channel.

9. The dual needle delivery system that connects and deploys needles of a medication delivery device of claim 1, further comprising
    a curved channel through which said second needle travels when said needle sled moves from said retracted position to said deployed position, causing said second needle to change orientation from substantially parallel to said skin of said user in said retracted position to non-parallel with said skin of said user in said deployed position.

10. The dual needle delivery system that connects and deploys needles of a medication delivery device of claim 9, wherein
    when said needle sled is in said deployed position, the second needle is propelled into the skin of said user at an angle of needle insertion to a surface of said skin of greater than or equal to 30 degrees and less than 90 degrees.

* * * * *